(12) United States Patent
Paul, III (10) Patent No.: US 7,888,031 B2
(45) Date of Patent: *Feb. 15, 2011

(54) DETECTION OF POLYKETIDE SYNTHETASE GENE EXPRESSION IN KARENIA BREVIS

(75) Inventor: John H. Paul, III, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/206,385

(22) Filed: Sep. 8, 2008

(65) Prior Publication Data

US 2009/0075286 A1 Mar. 19, 2009

Related U.S. Application Data

(62) Division of application No. 11/589,335, filed on Oct. 30, 2006, now Pat. No. 7,422,857.

(60) Provisional application No. 60/731,327, filed on Oct. 28, 2005.

(51) Int. Cl.
C12Q 1/68 (2006.01)
(52) U.S. Cl. .......................................... 435/6
(58) Field of Classification Search ........................ None
See application file for complete search history.

(56) References Cited

U.S. PATENT DOCUMENTS

| | | | |
|---|---|---|---|
| 5,420,011 A | 5/1995 | Manger et al. | |
| 5,582,983 A | 12/1996 | Anderson et al. | |
| 6,023,223 A | 2/2000 | Baxter, Jr. | |
| 6,071,859 A | 6/2000 | Ogawa et al. | |
| 6,171,626 B1 | 1/2001 | Lagos et al. | |
| 6,174,690 B1 | 1/2001 | Manger et al. | |
| 6,190,570 B1 | 2/2001 | Nakamura et al. | |
| 6,235,206 B1 | 5/2001 | Chan et al. | |
| 6,984,330 B2 | 1/2006 | Cushman et al. | |
| 7,205,112 B2 | 4/2007 | Paul, III et al. | |
| 2001/0025011 A1 | 9/2001 | Nagasaki et al. | |
| 2002/0029393 A1 | 3/2002 | Noren | |
| 2004/0005700 A1 | 1/2004 | Surber et al. | |
| 2004/0259095 A1 | 12/2004 | Cary et al. | |
| 2005/0209104 A1 | 9/2005 | Place et al. | |
| 2006/0132762 A1 | 6/2006 | Kirkpatrick et al. | |
| 2006/0159774 A1 | 7/2006 | Rigby | |
| 2007/0160983 A1 | 7/2007 | Paul, III et al. | |

FOREIGN PATENT DOCUMENTS

EP 0 329 822 B1 6/1994

OTHER PUBLICATIONS

Adachi, M. "Identification of the toxic dinoflagellates *Alexandrium catenella* and *A. tamarense* (Dinophyceae) using DNA probes and whole-cell hybridization" *J. Phycol.*, 1996, 32:1049-1052.

Casper, E. et al. "Development and evaluation of a method to detect and quantify enteroviruses using NASBA and internal control RNA (IC-NASBA)" *J. Virol. Methods*, 2005, 124:149-155.

Casper, E. et al. "Detection and quantification of the red tide dinoflagellate *Karenia brevis* by real-time nucleic acid sequence-based amplification" *App. Environ. Microbiol.*, Aug. 2004, 70(8):4727-4732.

Corredor, J.E. et al. "Geochemical rate-RNA integration study: ribulose-1,5-bisphosphate carboxylase/oxygenase gene transcription and photosynthetic capacity of planktonic photoautotrophs" *App. Environ. Microbiol.*, 2004, 70:5459-5468.

Culverhouse, P.F. et al. "Do experts make mistakes? A comparison of human and machine identification of dinoflagellates" *Mar. Ecol. Prog. Ser.*, 2003, 247:17-25.

Deflaun, M.F. et al. "Simplified method for dissolved DNA determination in aquatic environments" *App. Environ. Microbiol.*, 1986, 52:654-659.

Devereux, R. et al. "Development and applications of microbial ecogenomic indicators for monitoring water quality: Report of a workshop assessing the state of the science, research needs and future directions" *Environ. Monitoring and Assessment*, 2006, 116:459-479.

Donaldson, K.A. et al. "Detection, quantitation and identification of enteroviruses from surface waters and sponge tissue from the Florida Keys using real-time RT-PCR" *Water Res.*, 2002, 36:2505-2514.

Fang, X. et al. "Molecular beacons: Novel fluorescent probes" *Anal. Chem.*, 2000, 72:747A-753A.

Fang, X. et al. "Molecular beacons: Fluorogenic probes for living cell study" *Cell Biochem. Biophys.*, 2002, 37:71-81.

Godhe, A. et al. "Polymerase chain reaction in detection of *Gymnodinium mikimotoi* and *Alexandrium minutum* in field samples from Southwest India" *Mar. Biotechnol.*, 2001, 3:152-162.

Gray, M. et al. "Molecular detection and quantitation of the red tide dinoflagellate *Karenia brevis* in the marine environment" *Appl. Environ. Microbiol.*, 2003, 69:5726-5730.

Griffin, D.W. et al. "Pathogenic human viruses in coastal waters" *Clin. Microbiol. Rev.*, 2003, 16:129-143.

(Continued)

*Primary Examiner*—Nashaat T Nashed
(74) *Attorney, Agent, or Firm*—Saliwanchik, Lloyd & Eisenschenk (57) ABSTRACT

The present invention concerns an assay for the detection of polyketide synthetase (PKS) mRNA from the red tide dinoflagellate *Karenia brevis*. Another aspect of the invention concerns NASBA primers and a molecular beacon that enable detection of mRNA of one of the PKS genes. In another aspect, the present invention includes an internal control RNA (IC-RNA) that enables quantitative detection of the target as well as correction for inhibition of amplification. The assay of the invention provides a rapid and specific detection of the putative toxin-producing genes of the Florida Red Tide Organism. The assay of the invention is useful for determining the virulence of red tide blooms.

22 Claims, 4 Drawing Sheets

OTHER PUBLICATIONS

Griffin, D.W. et al. "Detection of viral pathogens by reverse transcriptase PCR and of microbial indicators by standard methods in the canals of the Florida Keys" *App. Environ. Microbiol.*, 1999, 65:4118-4125.

Jeffrey, W.H. and Paul, J.H. "Activity measurements of planktonic microbial and microfouling communities in a eutrophic estuary" *App. Environ. Microbiol.*, 1986, 51:157-162.

Jiang, S.C. and Paul, J.H. "Viral contribution to dissolved DNA in the marine environment as determined by differential centrifugation and kingdom probing" *App. Environ. Microbiol.*, 1995, 61:317-325.

Keightley, M.C. et al. "Real-time NASBA detection of SARS-associated coronavirus and comparison with real-time reverse transcription-PCR" *J. Med. Virol.*, 2005, 77:602-608.

Leone, G. et al. "Molecular beacon probes combined with amplification by NASBA enable homogeneous, real-time detection of RNA" *Nucleic Acids*, 1998, 26:2150-2155.

Lidie, K. et al. "Gene expression in Florida Red Tide dinoflagellate *Karenia brevis*: Analysis of an expressed sequence tag library and development of DNA microarray" *Mar. Biotechnol.*, 2005, 7:481-493.

Litaker, R.W. et al. "Identification of *Pfiesteria piscicida* (dinophyceae) and *Pfiesteria*-like organisms using internal transcribed spacer-specific PCR assays" *J. Phycol.*, 2003, 39:754-761.

Loret, P. et al. "No difference found in ribosomal DNA sequences from physiologically diverse clones of *Karenia brevis* (dinophyceae) from the Gulf of Mexico" *J. Plankton Res.*, 2002, 24:735-739.

Marras, S. et al. "Real-time assays with molecular beacons and other fluorescent nucleic acid hybridization probes" *Clin. Chim. Acta*, 2006, 363:48-60.

McDaniel, L. et al. "Evaluation of marine bacterial lysogens for development of a marine prophage induction assay" *Mar. Biotechnol.*, 2001, 3:528-535.

Millie, D.F. et al. "Detection of harmful algal blooms using photopigments and absorption signatures: A case study of the Florida Red Tide dinoflagellate, gymnodinium" *Limnol. Oceanogr.*, 1997, 42:1240-1251.

Örnólfsdóttir, E.B. et al. "Quantification of the relative abundance of the toxic dinoflagellate, *Karenia brevis* (dinophyta), using unique photopigments" *J. Phycol.*, 2003, 39:449-457.

Paul, J.H. et al. "Concentration of viruses and dissolved DNA from aquatic environments by vortex flow filtration" *App. Environ. Microbiol.*, 1991, 57:2197-2204.

Paul, J.H. et al. "Production of dissolved DNA, RNA, and protein by microbial populations in a Florida reservoir" *App. Environ. Microbiol.*, 1990, 56:2957-2962.

Paul, J.H. et al. "Amplification of the *rbcL* gene from dissolved and particulate DNA from aquatic environments" *App. Environ. Microbiol.*, 1990, 56:1963-1966.

Paul, J.H. et al. "Dynamics of extracellular DNA in the marine environment" *App. Environ. Microbiol.*, 1987, 53:170-179.

Patterson, S.S. et al. "A nucleic acid sequence-based amplification assay for real-time detection of norovirus genogroup II" *J. App. Microbiol.*, 2006, 101:956-963.

Patterson, S.S. et al. "Increased precision of microbial RNA quantification using NASBA with an internal control" *J. Microbiol Methods*, 2005, 60:343-352.

Peperzak, L. et al. Application and flow cytometric detection of antibody and rRNA probes to *Gymnodinium mikimotoi* (Dinophyceae) and *Pseudo-nitzschia multiseries* (Bacillariophyceae), 2000, pp. 206-209, in G.M. Hallegraff et al. Eds., Harmful algal blooms, IOC-UNESCO, Paris, France.

Pichard, S.L. et al. "Diversity of the ribulose bisphosphate carboxylase/oxygenase form I gene (*rbcL*) in natural phytoplankton communities" *App. Environ. Microbiol.*, 1997, 63:3600-3606.

Pichard, S.L. and Paul, J.H. "Gene expression per gene dose, a specific measure of gene expression in aquatic microorganisms" *App. Environ. Microbiol.*, 1993, 59:451-457.

Pichard, S.L. and Paul, J.H. "Detection of gene expression in genetically engineered microorganisms and natural phytoplankton populations in the marine environment by mRNA analysis" *App. Environ. Microbiol.*, 1991, 57:1721-1727.

Pierce, R.H. and Kirkpatrick, G.J. "Innovative techniques for harmful algal toxin analysis" *Environ. Toxicol. Chem.*, 2001, 20:107-114.

Rose, J.B. et al. "Comparison of PCR and plaque assay for detection and enumeration of coliphage in polluted marine waters" *App. Environ. Microbiol.*, 1997, 63:4564-4566.

Snyder, R.V. et al. "Polyketide synthase genes from marine dinoflagellates" *Mar. Biotechnol.*, 2003, 5:1-12.

Snyder, R.V. et al. "Localization of polyketide synthase encoding genes to the toxic dinoflagellate *Karenia brevis*" *Phytochemistry*, 2005, 66(15):1767-1780.

Stumpf, R.P. "Applications of satellite ocean color sensors for monitoring and predicting harmful algal blooms" *Hum. Ecol. Risk Assess.*, 2001, 7:1363-1368.

Tyagi, S. and Kramer, F. "Molecular beacons: probes that fluoresce upon hybridization" *Nature Biotech.*, 1996, 14:303-308.

Tyagi, S. et al. "Multicolor molecular beacons for allele discrimination" *Nature Biotechnology*, 1998; 16:49-53.

Wawrik, B. et al. "Real-time PCR quantification of *rbcL* (ribulose-1,5-bisphosphate carboxylase/oxygenase) mRNA in diatoms and pelagophytes" *App. Environ. Microbiol.*, 2002, 68:3771-3779.

Griffin, D.W. et al. "Detection of viral pathogens by reverse transcriptase PCR and of microbial indicators by standard methods in the canals of the Florida Keys" *App. Environ. Microbiol.*, 1999, 65:4118-4125.

Jeffrey, W.H. and Paul, J.H. "Activity measurements of planktonic microbial and microfouling communities in a eutrophic estuary" *App. Environ. Microbiol.*, 1986, 51:157-162.

Jiang, S.C. and Paul, J.H. "Viral contribution to dissolved DNA in the marine environment as determined by differential centrifugation and kingdom probing" *App. Environ. Microbiol.*, 1995, 61:317-325.

Keightley, M.C. et al. "Real-time NASBA detection of SARS-associated coronavirus and comparison with real-time reverse transcription-PCR" *J. Med. Virol.*, 2005, 77:602-608.

Leone, G. et al. "Molecular beacon probes combined with amplification by NASBA enable homogeneous, real-time detection of RNA" *Nucleic Acids*, 1998, 26:2150-2155.

Lidie, K. at al. "Gene expression in Florida Red Tide dinoflagellate *Karenia brevis*: Analysis of an expressed sequence tag library and development of DNA microarray" *Mar. Biotechnol.*, 2005, 7:481-493.

Litaker, R.W. et al. "Identification of *Pfiesteria piscicida* (dinophyceae) and *Pfiesteria*-like organisms using internal transcribed spacer-specific PCR assays" J. Phycol., 2003, 39:754-761.

Loret, P. et al. "No difference found in ribosomal DNA sequences from physiologically diverse clones of *Karenia brevis* (dinophyceae) from the Gulf of Mexico" *J. Plankton Res.*, 2002, 24:735-739.

Marras, S. et al. "Real-time assays with molecular beacons and other fluorescent nucleic acid hybridization probes" *Clin. Chim. Acta*, 2006, 363:48-60.

McDaniel, L. et al. "Evaluation of marine bacterial lysogens for development of a marine prophage induction assay" *Mar. Biotechnol.*, 2001, 3:528-535.

Millie, D.F. et al. "Detection of harmful algal blooms using photopigments and absorption signatures: A case study of the Florida Red Tide dinoflagellate, gymnodinium" *Limnol. Oceanogr.*, 1997, 42:1240-1251.

Millie, D.F. at al. "Using absorbance and fluorescence spectra too discriminate microalgal phylogentic grups and taxa" *J. Phycol.*, 2001, 37:35.

Örnólfsdóttir, E.B. et al. "Quantification of the relative abundance of the toxic dinoflagellate, *Karenia brevis* (dinophyta), using unique photopigments" *J. Phycol.*, 2003, 39:449-457.

SEQUENCE LISTING

<160> NUMBER OF SEQ ID NOS: 11

<210> SEQ ID NO 1
<211> LENGTH: 107
<212> TYPE: DNA
<213> ORGANISM: Artificial
<220> FEATURE:
<223> OTHER INFORMATION: target sequence within a K. brevis PKS gene
      (AT2-15L)

<400> SEQUENCE: 1
aatgctgctg gtgtcctcaa gaagggtttg acctctctca aggatgtgcc agttggagtt 60
ttctgtggcc aagctcagta tgattggagc aagatgcgcc tgcccat 107

<210> SEQ ID NO 2
<211> LENGTH: 107
<212> TYPE: DNA
<213> ORGANISM: Artificial
<220> FEATURE:
<223> OTHER INFORMATION: K. brevis PKS internal control RNA (IC-RNA)
sequence

<400> SEQUENCE: 2
aatgctgctg gtgtcctcaa gaagggtttg acctctctca aggatgtgcc agttgtggct 60
gcttatggtg acaatcagta tgattggagc aagatgcgcc tgcccat 107

<210> SEQ ID NO 3
<211> LENGTH: 64
<212> TYPE: DNA
<213> ORGANISM: Artificial
<220> FEATURE:
<223> OTHER INFORMATION: forward primer for PKS IC-RNA synthesis
(PKScalLt)

<400> SEQUENCE: 3
aatgctgctg gtgtcctcaa gaagggtttg acctctctca aggatgtgcc agttgtggct 60
gctt 64

<210> SEQ ID NO 4
<211> LENGTH: 63
<212> TYPE: DNA
<213> ORGANISM: Artificial
<220> FEATURE:
<223> OTHER INFORMATION: reverse primer for PKS IC-RNA synthesis
(PKScalRt)

<400> SEQUENCE: 4
atgggcaggc gcatcttgct ccaatcatac tgattgtcac cataagcagc cacaactggc 60
aca 63

<210> SEQ ID NO 5
<211> LENGTH: 20
<212> TYPE: DNA
<213> ORGANISM: Artificial
<220> FEATURE:
<223> OTHER INFORMATION: forward PKS-specific primer (PKSNASBA3)

<400> SEQUENCE: 5
gctgctggtg tcctcaagaa 20

<210> SEQ ID NO 6
<211> LENGTH: 49

-continued

```
<212> TYPE: DNA
<213> ORGANISM: Artificial
<220> FEATURE:
<223> OTHER INFORMATION: reverse PKS-specific primer (PKSNASBA4)

<400> SEQUENCE: 6
aattctaata cgactcacta tagggagagg gcaggcgcat cttgctcca                49

<210> SEQ ID NO 7
<211> LENGTH: 32
<212> TYPE: DNA
<213> ORGANISM: Artificial
<220> FEATURE:
<223> OTHER INFORMATION: PKS-specific molecular beacon (PKSBEACON2)

<400> SEQUENCE: 7
cgatcggagt tttctgtggc caagctcgat cg                                  32

<210> SEQ ID NO 8
<211> LENGTH: 32
<212> TYPE: DNA
<213> ORGANISM: Artificial
<220> FEATURE:
<223> OTHER INFORMATION: PKS-specific molecular beacon (PKSCALBEACON)

<400> SEQUENCE: 8
catgcgtggc tgcttatggt gacaatcgca tg                                  32

<210> SEQ ID NO 9
<211> LENGTH: 17
<212> TYPE: DNA
<213> ORGANISM: Artificial
<220> FEATURE:
<223> OTHER INFORMATION: M13 reverse primer

<400> SEQUENCE: 9
caggaaacag ctatgac                                                   17

<210> SEQ ID NO 10
<211> LENGTH: 20
<212> TYPE: DNA
<213> ORGANISM: Artificial
<220> FEATURE:
<223> OTHER INFORMATION: PKS-specific sequence of the PKSNASBA4 primer

<400> SEQUENCE: 10
ggcaggcgca tcttgctcca                                                20

<210> SEQ ID NO 11
<211> LENGTH: 107
<212> TYPE: DNA
<213> ORGANISM: Artificial
<220> FEATURE:
<223> OTHER INFORMATION: generic K. brevis PKS IC-RNA sequence
<220> FEATURE:
<221> NAME/KEY: misc_feature
<222> LOCATION: (56)..(75)
<223> OTHER INFORMATION: n is a, c, g, or t

<400> SEQUENCE: 11
aatgctgctg gtgtcctcaa gaagggtttg acctctctca aggatgtgcc agttgnnnnn  60
nnnnnnnnnn nnnnncagta tgattggagc aagatgcgcc tgcccat               107
```

DETECTION OF POLYKETIDE SYNTHETASE GENE EXPRESSION IN *KARENIA BREVIS*

CROSS-REFERENCE TO RELATED APPLICATIONS

The present application is a divisional of U.S. application Ser. No. 11/589,335, filed Oct. 30, 2006 now U.S. Pat. No. 7,422,857, which claims the benefit of U.S. Provisional Application Ser. No. 60/731,327, filed Oct. 28, 2005, each of which is hereby incorporated by reference herein in its entirety, including any figures, tables, nucleic acid sequences, amino acid sequences, and drawings.

GOVERNMENT SUPPORT

The subject matter of this application has been supported by research grants from the National Oceanic & Atmospheric Administration (NOAA) under grant numbers NA16OP1437 and NA06NOS4780230 and a research grant from the National Science Foundation under grant number BES-0216305. Accordingly, the government has certain rights in this invention.

BACKGROUND OF THE INVENTION

By conservative estimates, harmful algal blooms (HABs) cost the United States $50 million per year (Hoagland, P. et al. *Estuaries*, 2002, 25:819-837). Such estimates are based upon direct economic impacts on tourism, fisheries, etc., and do not account for irremediable costs such as those caused by mass marine mammal mortalities (Landsberg, J. H. *Rev. Fish. Sci.*, 2002, 10:113-390; Landsberg, J. H. and Steidinger, K. A. "A historical review of *Gymnodinium breve* red tides implicated in mass mortalities of the manatee (*Trichechus mantus latirostris*) in Florida, USA", 1998, pp. 97-100, in B. Reguera et al. Eds, Proceedings of the 8$^{th}$ International Conference on Harmful Algae, Xunta de Galicia and Intergovernmental Oceanographic Commission of UNESCO, Vigo Spain). Worldwide, algal toxins of all types may be responsible for as many as 60,000 human intoxication events per year (Van Dolah, F. M. et al. *Hum. Ecol. Risk Assess.*, 2001, 7:1329-1345).

Nearly all coastal regions of the United States are impacted by HABs for various intervals in time and intensity. Perhaps no coastal environment has a frequency of HABs equal to that of the Florida Gulf Coast, caused by the nonperidinin dinoflagellate *Karenia brevis* (Davis) cf. Hansen and Moestrup (=*Gymnodinium breve*). Although red tides have been observed in the Gulf of Mexico since the Spanish Conquests and reports of catastrophic fish mortalities go back to 1844, the identity of *K. brevis*, initially named *G. breve*, as the causative agent was not determined until the bloom of 1946 to 1947 (Gunther, G. et al. *Ecol. Monogr,* 1948, 18:311-324). In certain years, red tides have occurred during 12 months of the year, although they are most often encountered in the late summer and early fall, correlating with heavy rainfall (Landsberg, J. H. *Rev. Fish. Sci.*, 2002, 10:113-390).

There is a need for monitoring and prediction of HABs, and those of *K. brevis* are of particular concern. Historically, blooms have occurred primarily during the fall and winter months. However over recent years, the Florida red tide specifically and HABs in general appear to be more prevalent and wide-spread (Chretiennot-Dinet, M., *Oceanis*, 2001, 24:223-238; Hallegraeff, G. M., *Phycologia*, 1991, 32:79-99). Massive fish kills, marine mammal mortalities, human poisonings due to the consumption of tainted shellfish and complaints of respiratory irritations among beach-goers are associated with these blooms (Kirkpatrick et al., *Harmful Algae,* 2004, 3:99-115; Van Dolah et al., in Toxicology of Marine Mammals, Taylor & Francis, Inc., 2002, Vos et al. (Eds.), p. 247-269). These harmful effects are attributed to a suite of polyketide secondary metabolites known as brevetoxins, which are part of a larger family of dinoflagellate-derived polyketide toxins that pose a threat to human health. Brevetoxins are polyether ladder type compounds having two parent backbone structures, brevetoxin A and brevetoxin B, each with several side-chain variants. Examples of other harmful polyketide toxins include ciguatoxin, okadaic acid, and the related kinophysistoxins, pectenotoxins, yessotoxin, and the azaspiracids. The mechanism of synthesis of brevetoxins is unknown but is hypothesized to be the result of enzymes similar to polyketide synthetases. Recently, two polyketide synthetase genes were described from *K. brevis* (Snyder et al. *Mar. Biotechnol.,* 2003, 5:1-12; Snyder et al. *Phytochemistry,* 2005, 66(15): 1767-80).

A myriad of approaches have been taken to address the problem of HAB monitoring and prediction, including satellite ocean color sensing (Stumpf, R. P. *Hum. Ecol. Risk Assess.*, 2001, 7:1363-1368), photopigment analysis (Millie, D. F. et al. *Limnol. Oceanogr.,* 1997, 42:1240-1251; Millie, D. F. et al. *J. Phycol.,* 2001, 37:35; Oernolfsdottir, E. B. et al. *J. Phycol.,* 2003, 39:449-457), and toxin analysis (Pierce, R. H. and Kirkpatrick, G. J. *Environ. Toxicol. Chem.,* 2001, 20:107-114). Additionally, molecular methods are being developed to detect a variety of HAB species, including *Alexandrium* sp. (Adachi, M. et al. *J. Phycol.,* 1996, 32:1049-1052; Godhe, A. et al. *Mar. Biotechnol.,* 2001, 3:152-162), *Gymnodinium* sp. (Godhe, A. et al. *Mar. Biotechnol.,* 2001, 3:152-162; Peperzak, L. et al. "Application and flow cytometric detection of antibody and rRNA probes to *Gymnodinium mikimotoi* (Dinophyceae) and *Pseudo-nitzsehia multiseries* (Bacillariophyceae), 2000, pp. 206-209, in G. M. Hallegraff et al. Eds., Harmful algal blooms, IOC-UNESCO, Paris, France), *Pseudonitzschia* sp. (Peperzak, L. et al. "Application and flow cytometric detection of antibody and rRNA probes to *Gymnodinium mikimotoi* (Dinophyceae) and *Pseudo-nitzschia multiseries* (Bacillariophyceae), 2000, pp. 206-209, in G. M. Hallegraff et al. Eds., Harmful algal blooms, IOC-UNESCO, Paris, France), *Pfiesteria* sp., and *Pfiesteria*-like organisms (Litaker, R. W. et al. *J. Phycol.,* 2003, 39:754-761) as well as *K. brevis* (Gray, M. et al. *Appl. Environ. Microbiol.,* 2003, 69:5726-5730; Loret, P. et al. *J. Plankton Res.,* 2002, 24:735-739). All of these methods must be calibrated with microscopy-derived cell counts, which are prone to errors (Culverhouse, P. F. et al. *Mar. Ecol. Prog. Ser.,* 2003, 247:17-25).

Nucleic acid sequence-based amplification (NASBA) is an isothermal method of RNA amplification that has been previously used in clinical diagnostic testing. Recently, a real-time NASBA assay was developed for the detection of ribulose-1,5-bisphosphate carboxylase-oxygenase (RuBisCO) large-subunit (rbcL) mRNA from *K. brevis* (Casper et al., *Applied and Environmental Microbiology,* 2004, August, 70(8):4727-4732). The rbcL mRNA was selected as the target because cellular levels of mRNA are typically high and RNA degrades quickly in the environment, resulting in detection of viable *K. brevis* populations only. NASBA RNA amplification occurs at 41° C. (Davey et al., European Patent No. EP 0329822). RNA is amplified by use of an enzyme cocktail including T7 RNA polymerase, avian myeloblastosis virus reverse transcriptase, RNaseH, and two target-specific oligonucleotide primers.

Real-time detection of the amplicon was accomplished by use of a molecular beacon, a single-stranded oligonucleotide that forms a stem-loop structure (Tyagi and Kramer, *Nature Biotech.*, 1996, 14:303-308). The molecular beacon was labeled with 6-carboxy fluorescein (6-FAM) at its 5' end and quencher DABCYL at its 3' end. When the beacon is in the closed (hairpin loop) configuration the fluorophore is quenched. Upon binding to the amplicon, the quencher is separated from the fluorophore and the probe fluoresces. During the amplification reactions, the fluorescent signal is measured. The time at which the signal reaches exponential growth is defined as the time to positivity (TTP), which is analogous to the threshold cycle value in PCR. The TTP value is a function of how much initial target RNA is in the sample. This NASBA-based assay for *K. brevis* rbcL mRNA was used to successfully detect and quantify *K. brevis* in cultures and field samples collected from the coastal waters of southwest Florida.

BRIEF SUMMARY OF THE INVENTION

The present invention provides an amplification and detection technology for polyketide synthetase (PKS) gene expression from the red tide dinoflagellate *Karenia brevis* in samples, such as biological and environmental samples, based upon an enzymatic amplification reaction, such as nucleic acid sequence-based amplification (NASBA) or RT-PCR. The method of the invention is sensitive, rapid, and effective and may be used as an additional or alternative method to detect and quantify *K. brevis* in the marine environment.

NASBA is an isothermal method of amplifying RNA (Compton, J. *Nature*, 1991, 350(6313):91-92). The process results in an approximate billion-fold amplification of the RNA target in less than two hours and does not require the use of Taq polymerase or thermal cycling. It has been described as a self-sustained sequence reaction (3SR) (Guatelli et al., *Proc. Natl. Acad. Sci. USA*, 1990, 87(5):1874-1878) and transcription-based amplification (TAS) (Kwoh, D.Y. et al., *Proc. Natl. Acad. Sci. USA*, 1989, 86(4):1173-1177).

Key components of NASBA are the conversion of RNA into DNA by the action of reverse transcriptase and the production of RNA by T7 RNA polymerase. First, in the non-cyclic or linear phase of the reaction, a primer (P1) is bound at the 3' end of messenger RNA (mRNA). This primer is unusual in that it contains a T7 RNA polyrmerase promoter. Second, AMV reverse transcriptase converts the molecule to a RNA/DNA hybrid. RNAse H specifically degrades the RNA in the hybrid and the AMV reverse transcriptase converts the single stranded DNA into double stranded DNA. Finally, T7 RNA polymerase recognizes the T7 RNA polymerase promoter, initiating the cyclic phase. Antisense RNA product is produced and the AMV reverse transcript makes a DNA/RNA hybrid. RNAse H degrades the RNA, a duplex DNA molecule is synthesized, T7 RNA polymerase makes RNA, and the cycle continues.

The method combines current sample concentration and NASBA technology with novel nucleotide primers to amplify the dinoflagellate (*K. brevis*) RNA. Samples are obtained and can be concentrated by any method known in the art (for example, charged filters, filterite cartridges, vortex flow filtration, etc.) or, alternatively, left unconcentrated. The dinoflagellate RNA is extracted by a combination of heating and RNeasy extraction. Utilizing novel PKS-specific primers, the RNA can be amplified using NASBA technology. The RNA is then detected using a method known in the art (for example, by gel electrophoresis, molecular probing, or fluorescent molecular beacons).

In another aspect, the present invention provides primers, probes, molecular beacons, specific internal controls, and methods for detection and quantitation of *K. brevis* and *K. brevis* PKS in samples, such as biological or environmental samples. These methods (assays) are based upon the amplification of a portion of the *K. brevis* PKS gene, using a method such as NASBA for amplification, and detection using a labeled (e.g., fluorescently labeled) molecular beacon. The NASBA assay of the invention is very robust in amplification efficiency (e.g., counts of approximately 15-20 min. have been achieved), making it a very rapid analytical method.

In one embodiment, the sample is an environmental sample, such as water (e.g., salt water, fresh water, waste water, drinking water), sewage, sludge, and surfaces or samples obtained from surface swipes. In another embodiment, the sample is a biological specimen, such as a clinical sample (e.g., stool, saliva, blood, urine, cerebrospinal fluid, etc.). In another embodiment, the sample comprises an organism or tissue from an organism, such as shellfish.

Another aspect of the invention concerns NASBA primers and a molecular beacon that enable detection of mRNA of one of the PKS genes, identified herein as AT2-15L. In another aspect, the present invention includes an internal control RNA (IC-RNA) that enables quantitative detection of the target as well as correction for inhibition of amplification. The assay of the invention provides a rapid and specific detection of the putative toxin-producing genes of the Florida Red Tide Organism. Such an assay will be useful in determining the virulence of red tide blooms.

BRIEF DESCRIPTION OF THE SEQUENCES

SEQ ID NO:1 is a target sequence within a *K. brevis* PKS gene (AT2-15L).

SEQ ID NO:2 is a *K. brevis* PKS internal control RNA (IC-RNA) sequence.

SEQ ID NO:3 is a forward primer for PKS IC-RNA synthesis (PKScalLt).

SEQ ID NO:4 is a reverse primer for PKS IC-RNA synthesis (PKScalRt).

SEQ ID NO:5 is a forward PKS-specific primer (PKS-NASBA3).

SEQ ID NO:6 is a reverse PKS-specific primer (PKS-NASBA4).

SEQ ID NO:7 is a PKS-specific molecular beacon (PKS-BEACON2).

SEQ ID NO:8 is a PKS-specific molecular beacon (PKSCALBEACON).

SEQ ID NO:9 is the M13 reverse primer.

SEQ ID NO:10 is the PKS-specific sequence of PKS-NASBA4 primer (SEQ ID NO:6).

SEQ ID NO:11 is a generic *K. brevis* PKS IC-RNA sequence (similar to SEQ ID NO:2), in which the enterovirus beacon binding site is replaced with any sequence that does not partially or fully hybridize with the target PKS sequence. Thus, "n" can be any nucleotide, as long as the sequence of "n" nucleotides does not fully or partially hybridize with the target PKS sequence.

DETAILED DESCRIPTION OF THE INVENTION

This present invention concerns an amplification assay of the mRNA of the K. brevis polyketide synthetase (PKS) gene. The assay of the invention, and the primers, molecular beacons, and internal control RNA (IC-RNA) used therein, provide a rapid determination of *K. brevis* toxin gene activity, enabling prediction of fish kills and the determination of relative virulence of a *K. brevis* bloom. In one embodiment, the target *K. brevis* PKS gene corresponds to the gene identified herein as AT2-15L (Snyder et al., *Phytochemistry*, 2005, 66:1767-1780). In a specific embodiment, the polynucleotide region of SEQ ID NO:1 is targeted. However, other regions of the *K. brevis* PKS gene can be targeted, and other *Karenia* PKS genes can be targeted, in accordance with the present invention. For example, in another embodiment, the target PKS gene corresponds to the gene identified as AT2-10L (Snyder et al., *Phytochemistry*, 2005, 66:1767-1780).

The subject invention provides polynucleotides and methods for detecting the presence of *K. brevis* PKS RNA, within a sample. The method of the invention can include a series of biochemical steps preparatory to commencing the detection assay. In one embodiment, the invention provides an isolated polynucleotide comprising a nucleic acid sequence selected from the group consisting of SEQ ID NOs: 2, 3, 4, 5, 6, 7, 8, 10, and 11, or a functional fragment thereof. In another embodiment, the invention provides an isolated polynucleotide consisting of a nucleic acid sequence selected from the group consisting of SEQ ID NOs: 2, 3, 4, 5, 6, 7, 8, 10, and 11, or functional fragments of any of the foregoing.

In one embodiment, the method of the invention comprises contacting a polynucleotide region of the polyketide synthetase gene of *Karenia brevis* with amplification primers; amplifying the polynucleotide region of the polyketide synthetase gene; and detecting the presence of an amplified polynucleotide, wherein the presence of the amplified polynucleotide is indicative of the presence of *Karenia brevis* in the sample.

The method of the invention includes amplifying the PKS RNA from the sample using an isolated polynucleotide (amplification primer and/or beacon) of the invention, which is capable of selectively hybridizing with the target nucleic acids. Preferably, the polynucleotides are selected from the group consisting of SEQ ID NOs: 5, 6, 7, and 8, or functional fragments of any of the foregoing.

Samples are obtained and are tested, either unconcentrated or after concentration by a method known in the art (for example, charged filters, filterite cartridges, vortex flow filtration, etc). Current sample concentration and NASBA technology is combined with novel nucleotide primers to amplify the PKS RNA contained therein. The PKS RNA can be extracted by a combination of heating and RNeasy extraction. Utilizing novel PKS primers, the RNA is amplified using NASBA technology or other enzyme-based amplification reaction.

The method of the subject invention involves obtaining or providing a sample (also referred to herein as the test sample). The test sample can be taken from anywhere that may contain *K. brevis*, for which there is a desire to detect the presence of the dinoflagellate or its toxin. For instance, such a test sample can be taken from a human or non-human subject, such as a companion animal (such as a dog or cat), drinking water, or livestock (e.g., bovine, porcine, etc.) facilities, livestock drinking water, the surrounding environment (pastures, water, etc.), from environmental specimens, from aquatic media in direct or indirect contact with the source of contamination, for example, coastal or other marine waters, shellfish beds, rivers close to the source of contamination or crossing the possible source of contamination, food for humans, shellfish and fish meats, food for companion animals, food for livestock, etc. The test sample can be surface matter that may contain or otherwise support the presence of the dinoflagellate.

The sample can be any sample that may contain the dinoflagellate. For example, the test sample can be a biological sample, such as blood, saliva, urine, sputum, nasal mucus, feces (stool), host cells, host tissues, tissue homogenates, muscle, liver, thymus, cerebrospinal fluid, etc.; or an environmental sample such as a salt water, fresh water, or brackish water sample, a sample of fish or molluscs found in potentially contaminated water, clothing, eating utensils, etc. In one embodiment, the sample comprises ship ballast water. The samples can be subjected to purifying protocols known in the art or used in the detection analysis directly. For example, column chromatography, density centrifugation, or ammonium sulfate precipitation. These and other methods are disclosed, for example, in Sambrook et al., Molecular Cloning: A Laboratory Manual, Cold Spring Harbor Laboratory, New York (1989). For simplicity and ease of assay, it is preferred that the sample be used directly without purification.

The test sample is then subjected to an appropriate treatment to remove or extract the nucleic acid contained in the dinoflagellate (*K. brevis*) potentially present in the sample. The RNA can be extracted by conventional methods, using conventional kits and reagents and then placed in contact with the reagents for amplification, e.g., NASBA, the reverse transcription (RT) reaction and for the polymerase chain reaction (PCR) in conditions in which a sequence of target nucleotides present in the genome of the dinoflagellate is amplified to form an amplification product. The RT-PCR reaction can be performed using conventional methods, either in a single stage or in two stages. Those skilled in the art are familiar with both alternatives.

RNA can be extracted from seawater via a variety of methods, particularly those described by Gray et al. (*App. Environ.*

*Microbiol.,* 2003, 69:5726-5730) and Casper et al. (*J. Vir. Methods,* 2005, 124:149-155). One method is described in Example 1.

As used herein, the term "primer" means an isolated or purified polynucleotide which is produced synthetically or biologically and includes a specific nucleotide sequence which permits hybridization to a section containing the target nucleotide sequence. Defined primers/polynucleotides may be produced by any of several well known methods, including automated solid-phase chemical synthesis using cyanoethylphosphoramidite precursors. Other well-known methods for construction of synthetic primers/oligonucleotides may, of course, be employed (J. Sambrook, E. F. Fritsch and T. Maniatis, Molecular Cloning 11 (2d ed. 1989).

The primers and molecular beacons used to amplify the sample nucleic acids (e.g., SEQ ID NOs: 4, 5, 6, 7, and 8, or functional fragments of any of the foregoing) may be coupled to a detectable moiety (a label). A preferred example of such a detectable moiety is fluorescein, which is a standard label used in nucleic acid sequencing systems using laser light as a detection system. Other detectable labels can also be employed to label the primers, molecular beacons, and probes of the invention, however, including other fluorophores, radio labels, chemical couplers such as biotin which can be detected with streptavidin-linked enzymes, and epitope tags such as digoxigenin detected using antibodies. The primers, probes, and molecular beacons may be modified whereby another nucleotide is added to or substituted for at least one nucleotide in the oligonucleotide. The term "add(ed)" means that nucleotide, oligo dGTP, oligo DATP, oligo dTTP, oligo dCTP, etc. having fluorescence substance, linker arm, biotin, etc. are bound to a 5'-terminal or a 3'-terminal of the oligonucleotide sequence. The term "substitute(d)" means that nucleotide(s) having a fluorescence substance, linker arm, biotin, etc. is introduced as a substitute for at least one nucleotide in the oligonucleotide. Introduction of known labels such as radioactive substances, enzymes, fluorescence substances, etc. after synthesis of the oligonucleotide is also included therein.

The reagent mix to perform the RT of the RNA of the dinoflagellate (*K. brevis*) contains the reagents required for the reaction, for example water, dNTPs (dATP, dCTP, dGTP and dTTP), an appropriate buffer for the RT reaction, a reverse transcriptase, an initiator oligonucleotide (also known as a primer) which binds with a region of the RNA of the dinoflagellate and then, due to the reverse transcriptase, allows a DNA complementary (cDNA) to the RNA to be obtained, etc. On the other hand, the reagent mix for the PCR contains the reagents required for the reaction to take place, for example water, dNTPs, an appropriate buffer for the PCR reaction, a heat-stable polymerase DNA, a pair of primers to amplify the target PKS sequence, a magnesium salt, etc.

In another embodiment, the method of the invention is performed using a single RT-PCR reagent mix containing the reagents required for the reaction to take place, for example water, dNTPs, an appropriate buffer for the RT-PCR reactions, a reverse transcriptase, a heat-stable polymerase DNA, etc. There are kits commercially available that provide this reaction mix, to which the appropriate primers are added. In this case, it is an advantage that the primers used for the RT reaction is one of the primers involved in the enzymatic amplification reaction (PCR).

To apply the method provided by this invention, any primer that allows one to obtain a cDNA of the PKS can be used, and any pair of primers that allows amplification of a target sequence within the PKS gene can be used.

Conventional techniques can be used for the RT-PCR reaction, in conditions in which an amplifiable DNA fragment, eventually present in the reaction medium, representative of a target sequence of PKS, is amplified to form an amplification product. The amplification product is separated and analyzed using conventional techniques, for example by electrophoresis, and sequenced. Next, the presence or absence in the test sample of PKS is determined and the dinoflagellate isolate is identified. The identification of the isolate of the dinoflagellate detected can be by conventional methods, for example by sequencing the region of the amplified genome. The detection of a dinoflagellate in the test sample indicates the existence of environmental contamination or biological contamination (toxification).

Conventional techniques are used for the PCR, in conditions in which an amplifiable DNA fragment, eventually present in the reaction medium, representative of a target sequence PKS is amplified to form an amplification product. The amplification product is separated and analyzed using any conventional method, for example by electrophoresis, and sequenced, and the presence or absence of the dinoflagellate containing the selected PKS target sequence is determined and the dinoflagellate identified. The detection of a dinoflagellate in the test sample can indicate the existence of environmental or biological contamination, depending upon the nature and origin of the test sample. In a specific embodiment, the products of the RT-PCR reaction are separated by electrophoresis in agarose and viewed by conventional methods, for example ultraviolet light after staining with ethidium bromide.

The detection methods of the invention can be used in different applications, for instance to identify the existence of environmental contamination, or presence of toxification, to discover the origin of the contamination, to conduct epidemiological studies or studies related to dinoflagellate molecular evolution, etc.

Optionally, in the various embodiments of the invention, the method further comprises recording a determined number of *K. brevis* cells, *K. brevis* cell concentration, copies of PKS transcript (amplification product), number of copies of PKS per reaction, TTP ratio, or any combination of two or more of the foregoing, in physical or electronic media. Optionally, the aforementioned calculation(s) (also referred to herein as "outputs") include an annotation conveying the conditions under which the sample was collected or the conditions under which the determination was made, such as temperature or salinity. In one embodiment, the number of PKS copies is measured and input into a computer algorithm that then calculates number of *K. brevis* cells or *K. brevis* cell concentration. Optionally, the outputs can be displayed on an output device, such as an analog recorder, teletype machine, typewriter, facsimile recorder, cathode ray tube display, computer monitor, or other computation device. Optionally, the displayed outputs include an annotation conveying the conditions under which the sample was collected or the conditions under which the determination was made (such as temperature or salinity).

Optionally, in the various embodiments of the invention, the method further comprises carrying out a manipulation of the sample or the source of the sample (e.g., a water body) based on one or more of the outputs. The manipulation can comprise, for example, application of a substance or treatment that controls, eliminates, or neutralizes the dinoflagellate or its neurotoxin(s) (see, for example, U.S. Pat. No. 6,984,330 (Cusluman et al.), which describes a method for controlling *K. brevis* with low concentrations of ozone; and U.S. patent application publication 20060159774 (Rigby), which describes a method for killing and managing red tide using a composition comprising sodium hypochlorite).

Optionally, in the various embodiments of the invention, the method further comprises comparing one or more of the outputs, as determined above, to pre-existing output data from samples taken from the same source or a different source. The pre-existing data from a sample may be that observed under particular conditions (e.g., temperature, salinity), for example.

Optionally, in the various embodiments of the invention, the method further comprises introducing a test agent to the sample, to the source from which the sample was taken, or to a different sample, before, during, or after determining one or more of the calculations (e.g., number of *K. brevis* cells, *K. brevis* cell concentration, copies of PKS transcript, number of copies of PKS per reaction, TTP ratio, or any combination of two or more of the foregoing), in order to determine whether the test agent exerts a biological effect on the dinoflagellates or its neurotoxin(s).

The present invention can be used in conjunction with other assays for determining the presence of *K. brevis* or other dinoflagellates, or their toxins, in a sample (see, for example, U.S. patent application publication 20060132762 (Kirkpatrick et al.), which describes an optical phytoplankton discriminator). In assays of field samples for PKS, samples that were positive for *K. brevis* rbcL mRNA were also positive for the *K. brevis* PKS gene AT2-15L mRNA, and those that lacked one lacked the other, indicating a strong co-occurrence of these genes.

The invention further includes a kit for the detection of *K. brevis*, comprising at least a pair of primers allowing one to amplify a target sequence of the cDNA of the dinoflagellate.

The kits provided by this invention can be in pack-form containing a plurality of recipients (e.g., compartments), including recipients with one or more primers, probes, IC-RNAs, and/or labeled molecular beacons of the subject invention (e.g., SEQ ID NOs:2, 3, 4, 5, 6, 7, 8, 10, 11, or functional fragments of any of the foregoing), recipients with all or part of the other reagents required for the method provided by this invention, for example water, dNTPs (dATP, dCTP, dGTP and dTTP), an appropriate buffer for the reaction (RT, PCR or RT-PCR), a reverse transcriptase, a heat-stable polymerase DNA, a magnesium salt, etc. Additionally and optionally, the kits provided by this invention can include recipients with nucleic acid (RNA, cDNA, DNA, etc.) from *K. brevis*, e.g., *K. brevis* PKS, well characterized for use as a positive control. In a specific embodiment, the control is a specific internal control of the subject invention, such as SEQ ID NO:2, or SEQ ID NO:11.

As indicated above, kits of the invention include reagents for use in the methods described herein, in one or more containers. The kits may include primers specific internal controls, and/or probes, buffers, and/or excipients, separately or in combination. Each reagent can be supplied in a solid form or liquid buffer that is suitable for inventory storage. Kits may also include means for obtaining a sample from a host organism or an environmental sample such as saltwater.

Kits of the invention can be provided in suitable packaging. As used herein, "packaging" refers to a solid matrix or material customarily used in a system and capable of holding within fixed limits one or more of the reagent components for use in a method of the present invention. Such materials include glass and plastic (e.g., polyethylene, polypropylene, and polycarbonate) bottles, vials, paper, plastic, and plastic-foil laminated envelopes and the like. Preferably, the solid matrix is a structure having a surface that can be derivatized to anchor an oligonucleotide probe, primer, molecular beacon, specific internal control, etc. Preferably, the solid matrix is a planar material such as the side of a microtitre well or the side of a dipstick. In one embodiment, the kit includes a microtitre tray with two or more wells and with reagents including primers, probes, specific internal controls, and/or molecular beacons in the wells.

The one or more primers, molecular beacons, or specific internal controls in the kit may be immobilized to the compartments. Methods for linking nucleic acid molecules to solid supports are well known in the art. Processes for linking the primer or probe to the solid matrix include amide linkage, amidate linkage, thioether linkage, and the introduction of amino groups on to the solid matrix. The kit may be conveniently adapted for automated or semi-automated use. The kit may include a plurality of primers, beacons, internal controls, probes, etc. that target either the 5' or 3' end of PKS, or the interior region of PKS, or both. Optionally, the primers, molecular beacons, specific internal controls, or probes are arrayed in the compartments of the kits.

Kits of the invention may optionally include a set of instructions in printed or electronic (e.g., magnetic or optical disk) form, relating information regarding the components of the kits and/or how to make various determinations (e.g., number of *K. brevis* cells, *K. brevis* cell concentration, copies of PKS transcript, number of copies of PKS per reaction, TTP ratio, or any combination of two or more of the foregoing). The kit may also be commercialized as part of a larger package that includes instrumentation for measuring other biochemical components, such as, for example, a mass spectrometer.

The terms "polynucleotide", "oligonucleotide", and "nucleic acid sequence" are used herein interchangeably to refer to nucleic acid sequences of any length. For example, DNA and/or RNA molecules are composed of various nucleotides and/or nucleotide analogs.

The term "fragments" as it relates to polynucleotides and nucleic acid molecules (including primers) is understood to mean those fragments which are specific for the particular target PKS sequence when used for methods to identify the presence of the dinoflagellate. For example, fragments of a polynucleotide of the subject invention (i.e., a primer, probe, molecular beacon, internal control) can be up to one nucleotide less than the particular full length sequence. For example, fragments can comprise a contiguous/consecutive span of at least 8, 9, 10, 11, 12, 13, 14, 15, and up to one nucleotide less than the full length nucleotide sequence of SEQ ID NOs:2, 3, 4, 5, 6, 7, 8, 10, and 11. In a specific embodiment, the fragments comprise a contiguous span of at least 18 nucleotides, and up to one nucleotide less than the full-length nucleotide sequence of SEQ ID NOs:2, 3, 4, 5, 6, 7, 8, 10, and 11. Fragments should be of sufficient length to retain their function according to the methods of the invention (to be "functional fragments"). For example, fragments of primers retain the ability to amplify their target sequence are functional fragments. In specific embodiments, the fragments have one, two, three, four, or five nucleotides less than the full length nucleotide sequence of the given polynucleotide. Such fragments may be truncated at the 5' end, the 3' end, or both the 5' and 3' ends, for example. Preferably, the fragments have no more than five nucleotides truncated in total (e.g., two nucleotide truncated from one end and three nucleotides truncated from the other). In a specific embodiment, the fragments comprise a contiguous span of at least 18 nucleotides of the 5' end of SEQ ID NOs:2, 3, 4, 5, 6, 7, 8, 10, and 11. In another specific embodiment, the fragments comprise a contiguous span of at least 18 nucleotides of the 3' end of SEQ ID NOs:2, 3, 4, 5, 6, 7, 8, 10, and 11.

An "isolated" or "purified" nucleic acid or an "isolated" or "purified" polypeptide is a nucleic acid or polypeptide that, by the hand of man, exists apart from its native environment and is therefore not a product of nature. An isolated nucleic acid or polypeptide may exist in a partially purified or substantially purified form. An isolated nucleic acid or polypeptide may also exist in a non-native environment such as, for example, a transgenic host cell. The polynucleotides of the invention (e.g., SEQ ID NOs: 2, 3, 4, 5, 6, 7, 8, 10, and 11) are preferably in an isolated or purified form.

The term "label" refers to any atom or molecule that may be used to provide a detectable (preferably, quantifiable) signal, and that may be attached to a nucleic acid or protein. Labels may provide signals detectable by fluorescence, radioactivity, colorimetry, gravimetry, X-ray diffraction or absorption, magnetism, enzymatic activity, and the like. For example, labels such as FAM (6-carboxyfluorescein), DABCYL (4-(4'-dimethylaminophenylazo)-benzoic acid), or other flurochromes may be utilized. For example, other flurochromes that can be added to the 5' end in place of FAM (e.g., in the beacon) include CRCG, Cy3, Cy5, Oregon Green, ROX, Texas Red, Cy 3.5, Cy 5.5, Hexachlorofluorescein, and TET. In place of DABCYL on the 3' end as a quencher, one can use Black Hole Quencher (BHQ), for example.

In one embodiment, the polynucleotides of the subject invention comprise a nucleic acid sequence selected from the group consisting of SEQ ID NOs:2, 3, 4, 5, 6, 7, 8, 10, and 11, or a functional fragment of SEQ ID NOs:2, 3, 4, 5, 6, 7, 8, 10, or 11, wherein the polynucleotide sequence includes a label at either the 5' end, the 3' end, or both the 5' and 3' ends.

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the reference sequence explicitly indicated.

The term "gene" is used to refer to any segment of nucleic acid associated with a biological function. The term "gene" encompasses the coding region of a protein, polypeptide, peptide or structural RNA (e.g., PKS gene). The term "gene" also includes sequences up to a distance of about 2 kb on either end of the coding region. These sequences are referred to as "flanking" sequences or regions (these flanking sequences are located 5' or 3' to the non-translated sequences present on the mRNA transcript). The 5' flanking region may contain control or regulatory sequences such as promoters and enhancers or other recognition or binding sequences for proteins that control or influence the transcription of the gene. The 3' flanking region may contain sequences that direct the termination of transcription, post-transcriptional cleavage and polyadenylation as well as recognition sequences for other proteins. A protein or polypeptide encoded in a gene may be full length or any portion thereof, so that all activities or functional properties are retained, or so that only selected activities (e.g., enzymatic activity, ligand binding, signal transduction, etc.) of the full-length protein or polypeptide are retained. The protein or polypeptide may include any sequences necessary for the production of a proprotein or precursor polypeptide. The term "gene" encompasses both cDNA and genomic forms of a coding region. A genomic form of a coding region may be interrupted with non-coding sequences termed "introns." The term "native gene" refers to gene that is naturally present in the genome of an untransformed cell. The primers of the subject invention amplify at least a portion of the PKS gene of the dinoflagellate to be detected within the sample.

The terms "coding region" or "coding sequence" refers to the nucleotide sequence that codes for a protein of interest (e.g., PKS) or to a functional RNA of interest, for example antisense RNA or a nontranslated RNA. The coding region of a protein is bounded on the 5' side by the nucleotide triplet "ATG" that encodes the initiator methionine and on the 3' side by one of the three triplets that specify stop codons (i.e., TAA, TAG, TGA). The coding region may be present in either a cDNA, genomic DNA or RNA form.

The terms "molecular beacon" and "labeled molecular beacon" refer to single-stranded oligonucleotide hybridization probes that form a stem-and-loop structure and can report the presence of specific nucleic acids in homogenous solutions (Tyagi and Kramer, *Nature Biotechnology*, 1996, 14:303-308; Fang et al., *Anal. Chem.*, 2000, 72:747a-753a; Fang et al., *Cell Biochem. Biophys.*, 2002, 37:71-81; Marras et al., *Clin. Clim. Acta*, 2006, 363:48-60; Keightley et al., *J. Med. Virol.*, 2005, 77:602-608; and Leone et al., *Nucleic Acids*, 1998, 26:2150-2155). They are particularly useful in situations where it is either not possible or desirable to isolate the probe-target hybrids from an excess of the hybridization probes, such as in real time monitoring of polymerase chain reactions in sealed tubes or in detection of RNAs within living cells. Molecular beacons are hairpin-shaped molecules with an internally quenched fluorophore whose fluorescence is restored when they bind to a target nucleic acid. They are designed in such a way that the loop portion of the molecule is a probe sequence complementary to a target nucleic acid molecule. The stem is formed by the annealing of complementary arm sequences on the ends of the probe sequence. A fluorescent moiety is attached to the end of one arm and a quenching moiety is attached to the end of the other arm. The stem keeps these two moieties in close proximity to each other, causing the fluorescence of the fluorophore to be quenched by energy transfer. Since the quencher moiety is a non-fluorescent chromophore and emits the energy that it receives from the fluorophore as heat, the probe is unable to fluoresce. When the probe encounters a target molecule, it forms a hybrid that is longer and more stable than the stem and its rigidity and length preclude the simultaneous existence of the stem hybrid. Thus, the molecular beacon undergoes a spontaneous conformational reorganization that forces the stem apart, and causes the fluorophore and the quencher to move away from each other, leading to the restoration of fluorescence. In order to detect multiple targets in the same solution, molecular beacons can be made in many different colors utilizing a broad range of fluorophores (Tyagi et al., *Nature Biotechnology*, 1998; 16: 49-53.) DABCYL, a non-fluorescent chromophore, serves as a universal quencher for any fluorophore in molecular beacons. Owing to their stem, the recognition of targets by molecular beacons is so specific that single-nucleotide differences can be readily detected.

The terms "comprising", "consisting of" and "consisting essentially of" are defined according to their standard meaning. The terms may be substituted for one another throughout the instant application in order to attach the specific meaning associated with each term.

As used in this specification and the appended claims, the singular forms "a", "an", and "the" include plural reference unless the context clearly dictates otherwise. Thus, for example, a reference to "a primer" includes more than one such primer. A reference to "a polynucleotide" includes more than one such polynucleotide, and the like.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

Following are examples that illustrate materials, methods, and procedures for practicing the invention. The examples are illustrative and should not be construed as limiting. Unless noted otherwise, all solvent mixture proportions are by volume and all percentages are by weight.

EXAMPLE 1

Filtration of Samples

Seawater samples are filtered onto Millipore Durapore filters (25 mm, 0.45 um pore size). The filters can be added to sterile 2.0 ml microfuge tubes, followed by 500-750 ul RLT buffer from the Qiagen RNeasy kit. Alternatively, samples can be filtered through 0.22 um Sterivex-GV filters, and RLT buffer added directly to the cartridge. Tubes are capped and sterivex cartridges are also capped. If the RNA cannot be extracted immediately, the samples are frozen in liquid nitrogen and then stored in a −80° freezer. The RNA is extracted following the RNeasy kit protocol using the RNeasy reagents (Qiagen). Alternatively, other RNA extraction protocols (i.e., Xtrabind by Xtrana Corporation) may be used.

Finally, water samples can be filtered directly onto nucleic acid purification columns as made by Stratagene or those found in the RNeasy kit (Qiagen). The extraction of RNA can be carried out following the manufacturer's instructions.

EXAMPLE 2

IC-RNA Design and Synthesis

An Internal Control RNA (IC-RNA) was designed to provide internal calibration of each assay and to correct for between-reaction variation. The IC-RNA molecule was designed to be identical to the PKS target sequence of the NASBA assay with the exception that the primer binding site has been replaced with the enterovirus beacon binding site (Table 1). However, any known (pre-determined) sequence that does not fully or partially hybridize with the target PKS sequence can be used instead of the enterovirus beacon binding site. To synthesize the IC-RNA molecule, two oligonucleotide primers were designed to span the entire sequence with a 20-bp overlap sequence (Table 2). These oligonucleotides were placed in a PCR reaction (100 pmols each) and run under the standard PCR conditions with an annealing step of 50° C. for 30 cycles. Products were visualized on a 1% agarose gel stained with ethidium bromide. Amplicons were cloned using the TA-TOPO pCRII cloning kit (Invitrogen Corp., Carlsbad, Calif.) according to manufacturer's instructions. PCR amplification using the upstream M13 reverse primer (5'-CAGGAAACAGCTAT(JAC-3' SEQ ID NO:9) and the downstream PKS reverse primer (PKSNASBA4) was performed to determine insert size and directionality. Two clones appearing to have the insert in the correct orientation were grown overnight at 37° C. in LB supplemented with 50 ug/ml of Kanamycin. The plasmid was extracted using the Wizard Midi-plasmid purification kit (Promega Corp., Madison, Wis.). The plasmid was linearized by digestion with NotI at 37° C. overnight, and the enzyme removed with the Wizard DNA clean-up kit (Promega). Run-off transcripts were generated from an upstream SP6 promoter using the Riboprobe in vitro transcription kit (Promega). The transcripts were purified by the RNeasy spin protocol (Qiagen) and quantified with a Ribogreen RNA quantification kit (Molecular Probes, Inc., Eugene, Oreg.). Following quantification, transcript RNA was mixed 1:1 in an RNA storage buffer (8M guanidinium isothiocyanate, 80 mM Tris-HCL (pH 8.5), 24 mM $MgCl_2$, 140 mM KCl) and frozen at −80° C. until use. The IC-RNA is added to the NASBA primer mix so that an equal amount is included in each NASBA reaction. The ratio of the time it takes the target RNA to amplify above a threshold fluorescence to the time it takes the IC-RNA to amplify above that same threshold is defined as the time to positivity ratio (TTP ratio) and is used to increase the quantitative precision of the assay. The optimal concentration of PKS IC-RNA was determined to be 1 copies per reaction for standard curves ranging from $10^3$-$10^6$ copies of transcript or $10^0$-$10^3$ cells per reaction.

TABLE 1

*K. brevis* PKS and *K. brevis* PKS IC-RNA sequences.

| ID | Sequence | |
|---|---|---|
| *K. brevis* PKS sequence | AATGCTGCTGGTGTCCTCAAGAAGGGTTTGACCTCTCTCAAG GATGTGCCAGTTGG*AGTTTTCTGTGGCCAAGCT*CAGTATGATT GGAGCAAGATGCGCCTGCCCAT | (SEQ ID NO: 1) |
| *K. brevis* PKS IC-RNA sequence | AATGCTGCTGGTGTCCTCAAGAAGGGTTTGACCTCTCTCAAG GATGTGCCAGTTGT*GGCTGCTTATGGTGACAA*TCAGTATGATT GGAGCAAGATGCGCCTGCCCAT | (SEQ ID NO: 2) |

TABLE 2

Oligonucleotide sequences for PKS IC-RNA synthesis.

| Primer Designation | SEQUENCE | |
|---|---|---|
| PKScalLt | AATGCTGCTGGTGTCCTCAAGAAGGGTTTGACCTCTCTCAAGG ATGTGCCAGTTGTGGCTGCTT | (SEQ ID NO: 3) |
| PKScalRt | ATGGGCAGGCGCATCTTGCTCCAATCATACTGATTGTCACCAT AAGCAGCCACAACTGGCACA | (SEQ ID NO: 4) |

In Table 1, the italicized sequences represent the beacon binding site of the PKS gene and IC-RNA, respectively. The underlined sequences in Table 1 represent binding sites of the amplification primers PKSNASBA3 and PKSNASBA4.

The present invention also provides a generic *K. brevis* PKS IC-RNA:

(SEQ ID NO: 11)
AATGCTGCTGGTGTCCTCAAGAAGGGTTTGACCTCTCTCAAGGATG

TGCCAGTTGNNNNNNNNNNNNNNNNNNNNNCAGTATGATTGGAGCAAGATG

CGCCTGCCCAT.

SEQ ID NO: 11 is a generic *K. brevis* PKS IC-RNA sequence (similar to SEQ ID NO:2), in which the 20-nucleotide enterovirus beacon binding site is replaced with any sequence that does not partially or fully hybridize with the target PKS sequence. Thus, "n" can be any nucleotide, as long as the sequence of "n" nucleotides does not fully or partially hybridize with the target PKS sequence.

EXAMPLE 3

Real Time NASBA using PKS specific Primers and Molecular Beacons

The sequences of the primers and beacons appear in Table 3. These will result in a 101 bp amplicon.

TABLE 3

| Primer Designation | Sequence | Binding Site in AT2-15L |
|---|---|---|
| PKSNASBA3 | GCTGCTGGTGTCCTCAAGAA (SEQ ID NO: 5) | 68-87 |
| PKSNASBA4 | *AATTCTAA TACGACTC ACTATAGGG*AGA-GGCAGGCGCATCTTGCTCCA (SEQ ID NO: 6) | 150-169 |
| PKSBEACON2 | 6FAM-CGATCGGAGTTTTCTGTGGCCAAGCTCGATCG-DABCYL (SEQ ID NO: 7) | 120-139 |
| PKSCALBEACON | 6ROX-CATGCGTGGCTGCTTATGGTGACAATCGCATG-DABCYL (SEQ ID NO: 8) | 120-139 |

In Table 3, the italicized sequence represents the T7 RNA polymerase promoter in PKSNASBA4. The sequence in bold in Table 3 represents a purine-rich sequence in PKSNASBA4. The underlined sequence (GGCAGGCGCATCTTGCTCCA (SEQ ID NO:10)) represents the PKS-specific sequence.

Table 4 shows the co-occurrence of PKS mRNA with that of *K. brevis* cells detected by rbcL mRNA analysis.

| Station Name | Date | rbcL (+/−) | PKS (+/−) |
|---|---|---|---|
| SS2 | Dec. 16, 2005 | + | + |
| SS3 | Dec. 16, 2005 | + | + |
| WB | Dec. 16, 2005 | − | − |
| RP | Jan. 4, 2006 | + | + |
| 9B | Aug. 25, 2006 | − | − |
| 3S | Aug. 25, 2006 | + | + |
| AM | Aug. 25, 2006 | + | + |
| PS | Aug. 25, 2006 | + | + |
| SFP | Aug. 25, 2006 | + | + |
| NFP | Aug. 25, 2006 | + | + |
| MK | Aug. 25, 2006 | − | − |
| SS | Sep. 22, 2006 | + | + |
| NS | Sep. 22, 2006 | + | + |
| 3S | Sep. 22, 2006 | + | + |
| 7S | Sep. 22, 2006 | + | + |
| 6S | Sep. 22, 2006 | + | + |
| 9S | Sep. 22, 2006 | − | − |
| 13S | Sep. 22, 2006 | − | − |

Preferably, beacons and primers are purified (e.g., gel purified). 6FAM is 6 carboxyfluorescein.

For NASBA detection of *K. brevis* PKS mRNA, a standard curve of transcript (typically ranging from $10^3$-$10^6$ copies per reaction) or cells (typically ranging from $10^0$-$10^3$ cells per reactions) was employed. Each standard was run in duplicate. RNA from cells was extracted as above, and usually eluted from RNeasy columns in 50 μl of RNase-free water. Two and a half μl of eluate was used in NASBA reactions.

The following solutions are made in RNase-free water.

Beacons

PKSBEACON2 and PKSCALBEACON stocks are 100 µM stock, or 1.12 µg/µl. For NASBA, a dilution of 1:4.16 (=1 ul+3.16 ul DI) can be made to provide a 24 µM stock solution. A recommended final concentration is 100 nM.

Reagent Mix

Many of these reagents are available in the BioMerieux Nuclisens Basic NASBA kit (part number 285053).
1. Remove Reagent sphere tube from Nuclisens Kit.
2. Remove reagent sphere diluent from Nuclisens Kit.
3. Add 80 KCl of diluent to the lyophilized reagent sphere and immediately vortex well.
4. Mix KCl solution from Nuclisens Kit as follows: 16 µl KCl+13 µl NASBA water or any commercially available RNase-free water. Add the whole volume (29 µl) to the 80 µl diluted reagent sphere if 10 whole reactions or 23 half reactions are desired; other volumes can be calculated as desired.

Primer Mix+Beacon
1. Remove 1 tube of the primers BreveNASBA1 and BreveNASBA2 from freezer (each at a concentration of 100 µM). Dilute by adding 2 µl to 6 µl (1:4) RNAse-free water (makes primer concentrations of 25 µM).
2. Add 4 µl diluted primers BreveNASBA1 and BreveNASBA2, 1 µl PKSBeacon2 and PKSCALBEACON (24 µM) and 1 µl diluted IC-RNA (typically $10^7$ copies per reaction). This results in 10 µM each primer (final concentration of 400 nM) and 2.4 µM beacon (final concentration of 100 nM).
3. To your Reagent mixture (~109 µl) add 11 µl of the primer mixture.

Enzyme Cocktail
1. Remove red Enzyme Diluent from Nuclisens Kit in freezer and thaw.
2. Add 55 ul of the diluent to the Enzyme Accusphere from Nuclisens Kit. Do not vortex. Let this mixture sit while positive controls and cell extract are prepared.
3. After 20 minutes, mix the solution by gentle agitation (e.g., by flicking with Finger), spin down briefly in a microcentrifuge, and use within 1 hour.

NASBA Assay
1. Set up to 23 200 µl optical tubes.
2. Add 5 µl reagent/primer mix to each.
3. Add 2.5 µl of mRNA template (unknown or standard) or RNase-free water (controls).
4. Add optical caps to each tube.
5. Flick and spin in small microcentrifuge.
6. Using a standard thermal cycler Detection, set up a Precycle of 2 minutes @ 65° C. and 2 minutes @ 41° C. Insert the tubes and run the precycle.
7. When the cycle is complete, remove tubes and quickly set up a Real Time NASBA program in the bioMerieux EasyQ Detection system) and select a run time of 90 minutes. Immediately add 2.5 µl of the enzyme to a strip of caps. Add caps to the tube. Quickly spin, gently agitate (e.g., flick) tube, and spin again in small microcentrifuge.
8. Immediately put in the correct row in the EasyQ. Press Start.
9. When done, positive amplifications will appear as increases in fluorescence over blanks. A standard curve is generated from the TTP ratios and can be used to calculate the amount of *K. brevis* cells or PKS mRNA in the unknowns.
10. One can run a denaturing (formaldehyde) gel to verify amplification. The amplicon is ~100 base pairs (bp).

Results

Figure 1:
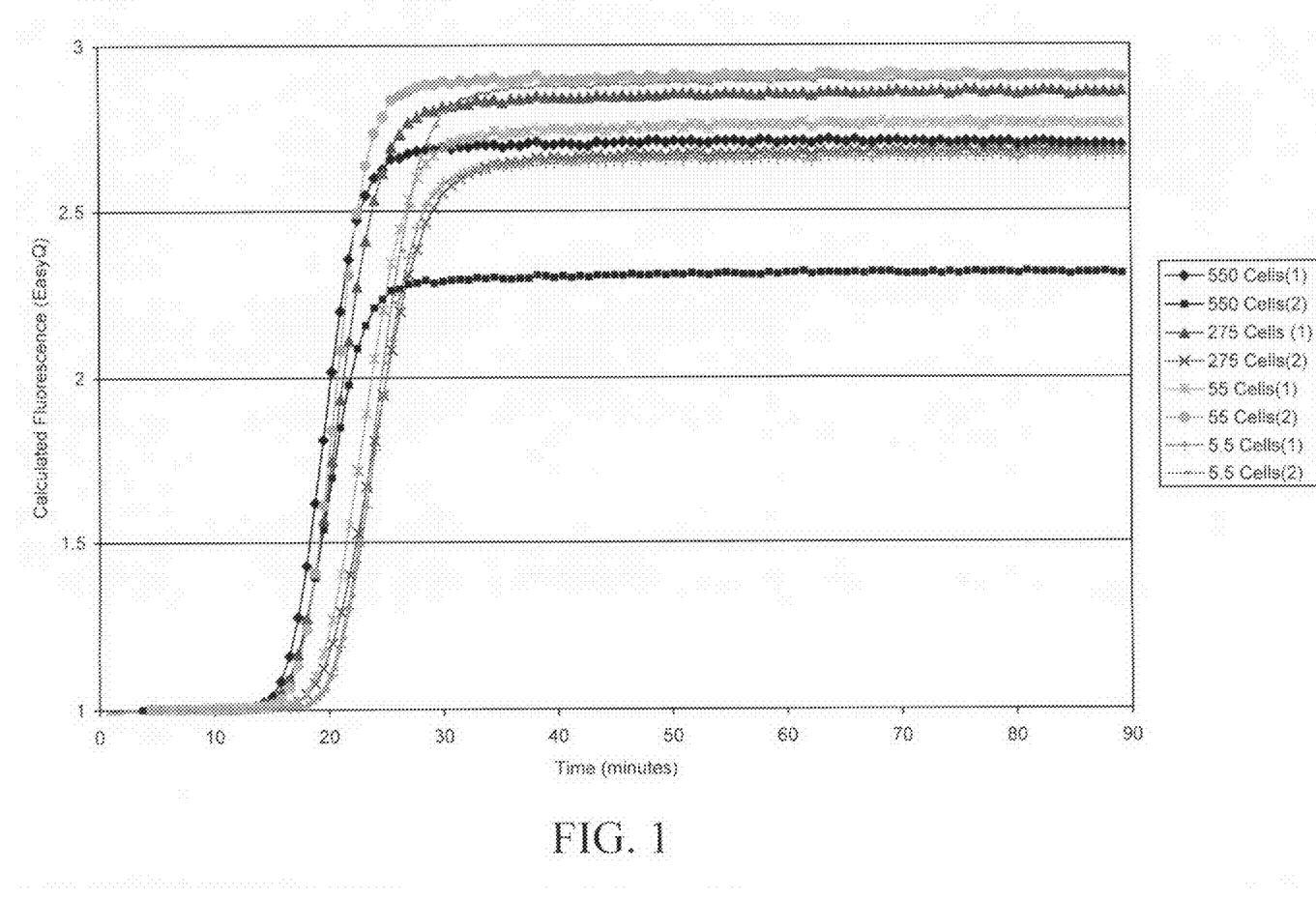
FIG. 1 is an amplification plot of *K. brevis* PKS mRNA using NASBA and an EasyQ Sequence detection system, but no IC-RNA. The data was transferred to an Excel spreadsheet. Fluorescence is plotted as a function of time for a dilution series of *K. brevis* cell RNA extract.
Figure 2:
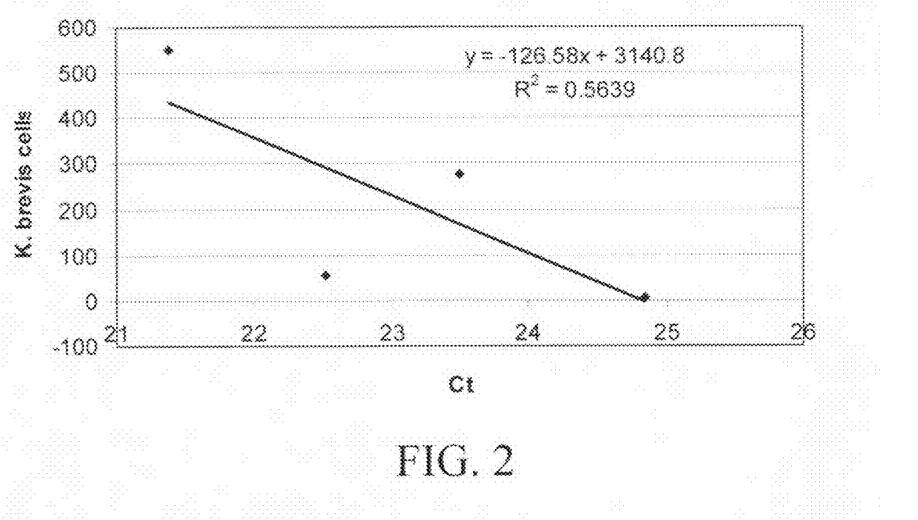
FIG. 2 is a plot of threshold cycle vs. concentration for detection of PKS in the absence of TC-RNA. The threshold cycle or Ct is the time at which amplification was detected, using the amplification curves of FIG. 1. Note that there is much noise in the data which can be dramatically reduced by inclusion of the IC-RNA in the assay (FIGS. 3 and 4).
Figure 3:
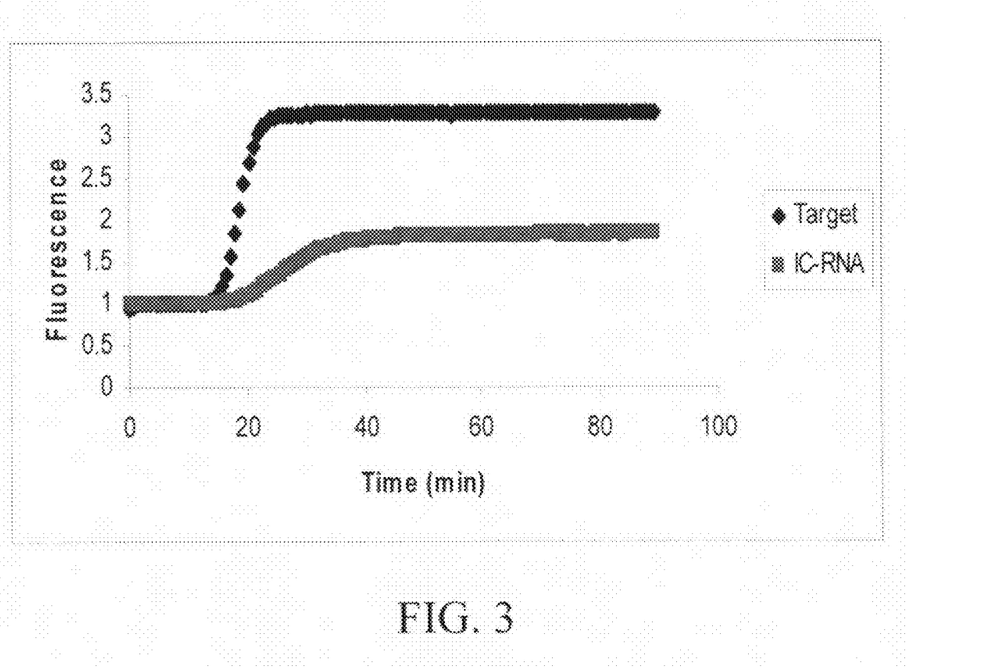
FIG. 3 is a standard amplification plot of a PKS NASBA reaction containing $10^5$ copies of PKS transcript and $10^7$ copies of IC-RNA.
Figure 4:
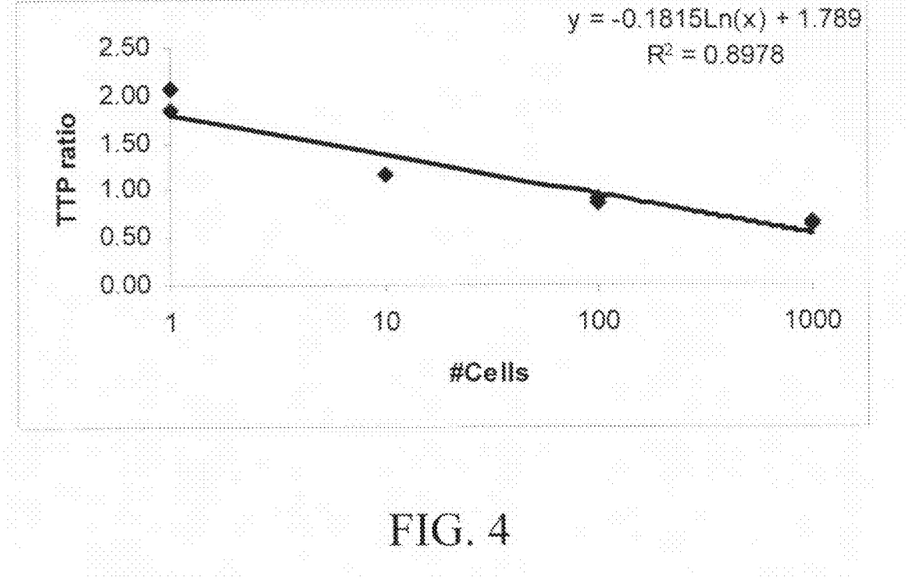
FIG. 4 is a plot of cell concentration vs. TTP ratio for a standard curve of *K. brevis* cells. The TTP ratio is the ratio of the times to positivity (or Ct) of the unknown or standard and the IC-RNA. The IC-RNA corrects for tube to tube variability and the presence of inhibitors in the amplification reaction
Figure 5:
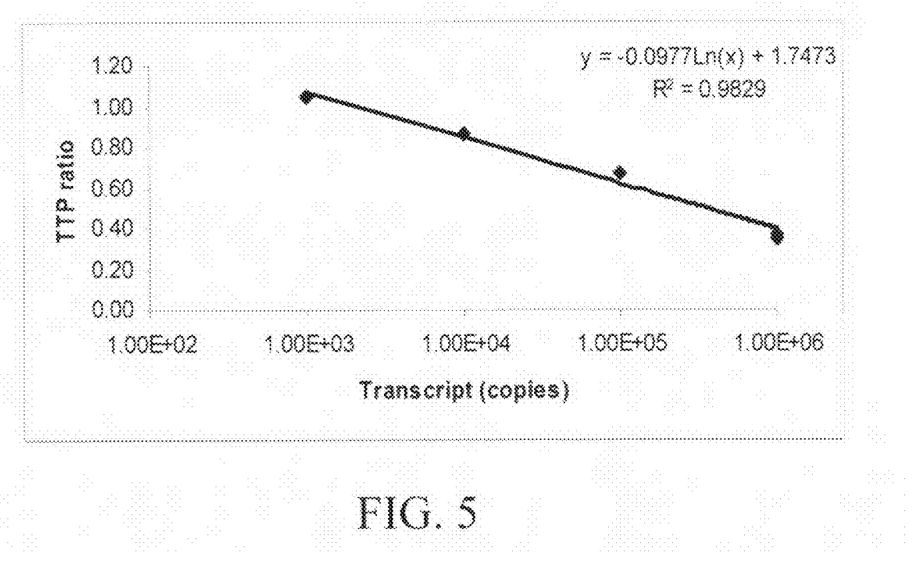
FIG. 5 is a plot of transcript copy number vs. TTP ratio. This data is analogous to that of FIG. 4 but uses purified in vitro generated transcript rather than *K. brevis* cell extracts.
Figure 6:
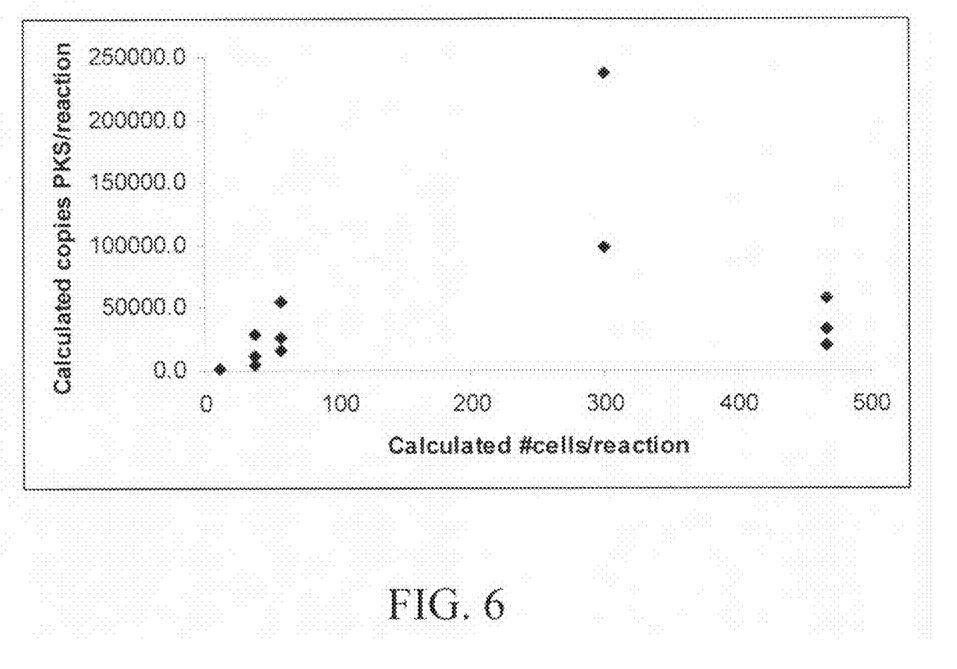
FIG. 6 is a plot of the calculated number of cells per reaction based on the rbcL NASBA assay vs. the calculated number of copies of PKS per reaction in several bloom samples. Note that optimal PKS mRNA levels occurred at intermediate cell abundances.

FIG. 1 is an amplification plot of *K. brevis* PKS mRNA using NASBA and an EasyQ Sequence detection system but no IC-RNA. The data was transferred to an Excel spread sheet. Fluorescence is plotted as a function of time for a dilution series of a *K. brevis* cell RNA extract. FIG. 2 is a plot of threshold cycle vs. concentration for detection of PKS in the absence of IC-RNA. FIG. 3 is a standard amplification plot of a PKS NASBA reaction containing $10^5$ copies of PKS transcript and $10^7$ copies of IC-RNA. FIG. 4 is a plot of cell concentration vs. TTP ratio for a standard curve of *K. brevis* cells. FIG. 5 is a plot of transcript copy number vs. TTP ratio. FIG. 6 is a plot of the calculated number of cells per reaction based on the rbcL NASBA assay vs. the calculated number of copies of PKS per reaction in several bloom samples.

Table 5 shows PKS genes most closely related to the *K. brevis* PKS gene.

TABLE 5

| Accession Number | Length in nt | Organism |
| --- | --- | --- |
| AAEE010000 | 720 | *Cryptosporidium parvum* |
| AAHF010000 | 750 | *Aspergillus fumigatus* Af293 |
| AAJL010000 | 720 | *Burkholderia ambifaria* AMMD |
| AB032549 | 656 | *Microcystis aeruginosa* |
| AE000516 | 720 | *Mycobacterium tuberculosis* CDC1551 |
| AY604655 | 680 | *Symploca* sp. HPC-3 |
| AY652953 | 720 | *Lyngbya majuscula* |
| AY857366 | 719 | uncultured *Porifera* |
| AY857383 | 707 | bacterium JL123 |
| AY857384 | 711 | bacterium JL048 |
| AY857391 | 719 | bacterium K610 |
| AY857395 | 707 | bacterium M548 |
| AY857397 | 707 | fungal sp. M565 |
| BA000019 | 709 | *Nostoc* sp. PCC 7120 |
| MLI557546 | 670 | *Melittangium lichenicola* |
| NZ_AAAY020 | 680 | *Nostoc punctiforme* PCC 73102 |
| NZ_AABN020 | 570 | *Desulfovibrio desulfuricans* G20 |
| NZ_AADV020 | 671 | *Crocosphaera watsonii* WH 8501 |

The NASBA assay of the invention is very robust in amplification efficiency (e.g., counts of approximately 15-20 min. have been achieved), making it a very rapid analytical method. In assays of field samples for PKS, samples that were positive for *K. brevis* rbcL mRNA were also positive for the *K. brevis* PKS gene AT2-15L mRNA, and those that lacked one lacked the other, indicating a strong co-occurrence of these genes.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A method for detecting the presence of *Karenia brevis* in a sample, comprising contacting a polynucleotide region of the polyketide synthetase gene of *Karenia brevis* with amplification primers, wherein the amplification primers comprise one or more of SEQ ID NO:5, SEQ ID NO:6, or SEQ ID NO:10; amplifying the polynucleotide region of the polyketide synthetase gene; and detecting the presence of an amplified polynucleotide, and wherein said method further comprises including an internal control (IC) nucleic acid during said amplifying step, wherein said IC nucleic acid comprises the nucleotide sequence shown in SEQ ID NO:2, wherein the presence of the amplified polynucleotide is indicative of the presence of *Karenia brevis* in the sample.

2. The method of claim 1, wherein the polynucleotide region of the polyketide synthetase gene comprises SEQ ID NO:1.

3. The method of claim 1, wherein said method further comprises contacting the polynucleotide region of the polyketide synthetase gene with a labeled molecular beacon.

4. The method of claim 3, wherein the labeled molecular beacon comprises SEQ ID NO:7.

5. The method of claim 1, wherein said amplifying comprises nucleic acid sequence based amplification (NASBA).

6. The method of claim 1, wherein said amplifying comprises RT-PCR.

7. The method of claim 1, wherein said detecting comprises hybridization of the amplified product with a probe.

8. The method of claim 1, wherein the sample is salt water.

9. The method of claim 1, wherein said method further comprises determining the quantity of amplified polynucleotide within the sample.

10. The method of claim 1, wherein said method further comprises subjecting the sample to a treatment to extract nucleic acid for assay in said method.

11. The method of claim 3, wherein the labeled molecular beacon comprises SEQ ID NO:8.

12. A method for detecting the presence of *Karenia brevis* in a sample, comprising contacting a polynucleotide region of the polyketide synthetase gene of *Karenta brevis* with amplification primers, wherein the amplification primers comprise one or more of SEQ ID NO:5, SEQ ID NO:6, or SEQ ID NO:10; amplifying the polynucleotide region of the polyketide synthetase gene; and detecting the presence of an amplified polynucleotide, and wherein said method further comprises including an internal control (IC) nucleic acid during said amplifying step, wherein said IC nucleic acid comprises the nucleotide sequence shown in SEQ ID NO:11, and wherein the sequence of "n" nucleotides does not fully or partially hybridize with the polyketide synthetase gene of *Karenia brevis*, wherein the presence of the amplified polynucleotide is indicative of the presence of *Karenia brevis* in the sample.

13. The method of claim 12, wherein the polynucleotide region of the polyketide synthetase gene comprises SEQ ID NO:1.

14. The method of claim 12, wherein said method further comprises contacting the polynucleotide region of the polyketide synthetase gene with a labeled molecular beacon.

15. The method of claim 14, wherein the labeled molecular beacon comprises SEQ ID NO:7.

16. The method of claim 12, wherein said amplifying comprises nucleic acid sequence based amplification (NASBA).

17. The method of claim 12, wherein said amplifying comprises RT-PCR.

18. The method of claim 12, wherein said detecting comprises hybridization of the amplified product with a probe.

19. The method of claim 12, wherein the sample is salt water.

20. The method of claim 12, wherein said method further comprises determining the quantity of amplified polynucleotide within the sample.

21. The method of claim 12, wherein said method further comprises subjecting the sample to a treatment to extract nucleic acid for assay in said method.

22. The method of claim 14, wherein the labeled molecular beacon comprises SEQ ID NO:8.

* * * * *

UNITED STATES PATENT AND TRADEMARK OFFICE
CERTIFICATE OF CORRECTION

PATENT NO. : 7,888,031 B2
APPLICATION NO. : 12/206385
DATED : February 15, 2011
INVENTOR(S) : John H. Paul, III It is certified that error appears in the above-identified patent and that said Letters Patent is hereby corrected as shown below:

Column 4,
Line 45, "TC-RNA" should read --IC-RNA--.

Column 5,
Line 55, "and II" should read --and 11--.

Column 8,
Line 65, "(Cusluman" should read --(Cushman--.

Column 14,
Line 20, "(5'-CAGGAAACAGCTAT(JAC-3'" should read --(5'-CAGGAAACAGCTATGAC-3'--.
Line 47, "be 1 copies" should be --be $10^7$ copies--.

Column 17,
Line 13, "80 KC1" should read --80 μl--.

Column 23,
Line 11, "wherein said. IC" should read --wherein said IC--.

Signed and Sealed this
Seventeenth Day of April, 2012

David J. Kappos
*Director of the United States Patent and Trademark Office*